(12) United States Patent
Korthout et al.

(10) Patent No.: US 7,807,711 B2
(45) Date of Patent: Oct. 5, 2010

(54) MEDICINAL ACIDIC CANNABINOIDS

(75) Inventors: Henricus Adriaan A. J. Korthout, Zaandijk (NL); Kitty Catharina M. Verhoeckx, Houten (NL); Rentje Frederik Witkamp, Wijk Bij Duurstede (NL); Robert Paul Doornbos, Ede (NL); Mei Wang, Oegstgeest (NL)

(73) Assignee: Nederlandse Organisatie voor Toegepast-Natuurwetenschappelijk Onderzoek TNO, Delft. (NL)

( * ) Notice: Subject to any disclaimer, the term of this patent is extended or adjusted under 35 U.S.C. 154(b) by 402 days.

(21) Appl. No.: 11/461,818

(22) Filed: Aug. 2, 2006

(65) Prior Publication Data

US 2007/0032544 A1    Feb. 8, 2007

Related U.S. Application Data

(63) Continuation of application No. PCT/NL2005/000075, filed on Feb. 2, 2005.

(30) Foreign Application Priority Data

Feb. 2, 2004    (EP)    .................... 04075300

(51) Int. Cl.
    *A61K 31/352* (2006.01)
(52) U.S. Cl. .................................. 514/454
(58) Field of Classification Search ............ 549/390; 562/469; 514/454
    See application file for complete search history.

(56) References Cited

U.S. PATENT DOCUMENTS

| 2002/0086438 A1* | 7/2002 | Elsohly et al. | 436/177 |
| 2004/0049059 A1* | 3/2004 | Mueller | 549/390 |

FOREIGN PATENT DOCUMENTS

| GB | 2 384 707 | 8/2003 |
| JP | 2000-078979 | * 3/2000 |
| WO | WO 89/01332 | 2/1989 |

OTHER PUBLICATIONS

Derwent-ACC-No. 2000-285930, Abstract of JP 2000-078979A published Mar. 21, 2000.*
Bhargava, "Potential Therapeutic Applications of Naturally Occurring and Synthetic Cannabinoids," *Gen. Pharmac.*, 9(4):195-213 (1978).
Izeboud et al., "Participation of β-Adrenergic Receptors on Macrophages in Modulation of LPS-Induced Cytokine Release," *J. Rec. Sign. Tr. Research*, 19(1-4):191-202 (1999).
Mosmann, "Rapid Colorimetric Assay for Cellular Growth and Survival: . . . ," *J Immunol. Methods*, 65:55-63 (1983).
Nagelkerken et al. "FcR Interactions Do Not Play a Major Role in Inhibition of Experimental Autoimmune Encephalomyelitis by Anti-CD154 Monoclonal Antibodies," *J. Immunol.*, 173:993-999 (2004).
Visser et al., "Increased Sensitivity to Glucocortoids in Peripheral Blood Mononuclear Cells of Chronic Fatigue Syndrome Patients . . . " *J. Investigative Medicine*, 49(2):195-204 (2001).
Yotoriyama, et al., "Comparison of Pharmacological Activity in Mice of Different Cannabis Extracts from CBDA and THCA Strains,", Eisai Kagaku, vol. 37 (6), p. 507-511 (1991).
Kinzer, et al., "The Fate of the Cannabinoid Components of Marihuana During Smoking," Bulletin on Narcotics, vol. XXVI, No. 3, Jul.-Sep. 1974, 41-54.
Stott, et al., "Cannabinoids for the Pharmaceutical Industry," Euphytica 140: 83-93, 2004.

* cited by examiner

*Primary Examiner*—Bernard Dentz

(57) ABSTRACT

The invention relates to an acidic cannabinoid for medical use and to a cannabis extract comprising an acidic cannabinoid. The extract may comprise one or more compounds selected from the group consisting of cannabidiolic acid (CBD-A), cannabidiol (CBD), cannabigerolic acid (CBGA), cannabigerol (CBG), cannabinolic acid (CBN-A) and cannabinol. The invention further relates to a method for preparing a preparation comprising extracting an acidic cannabinoid from cannabis.

15 Claims, 4 Drawing Sheets

Figure 2A
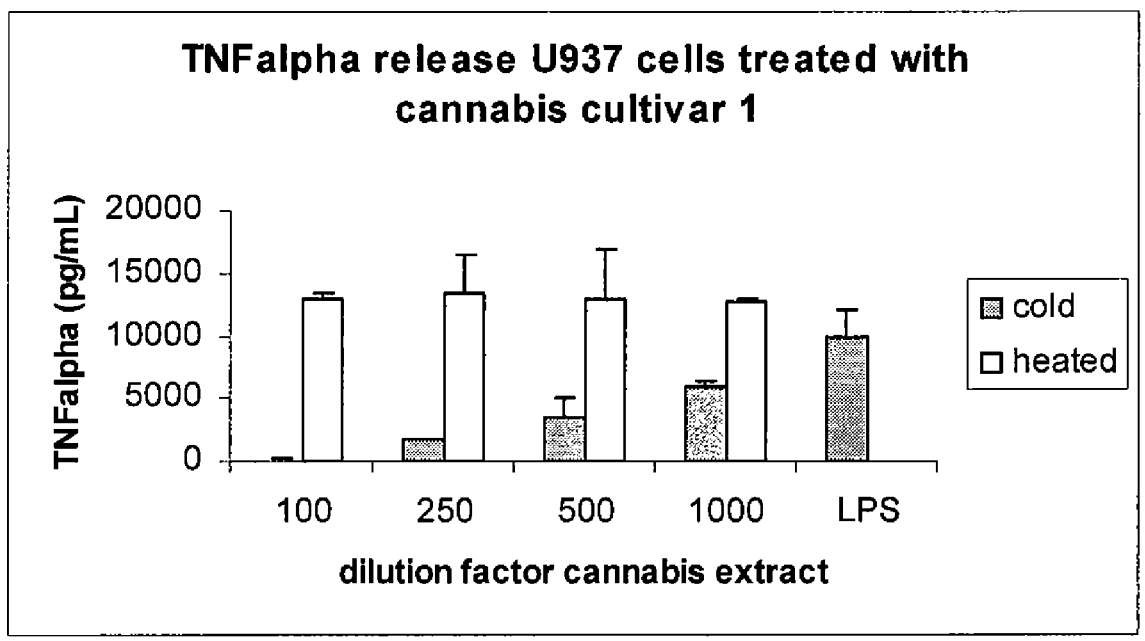
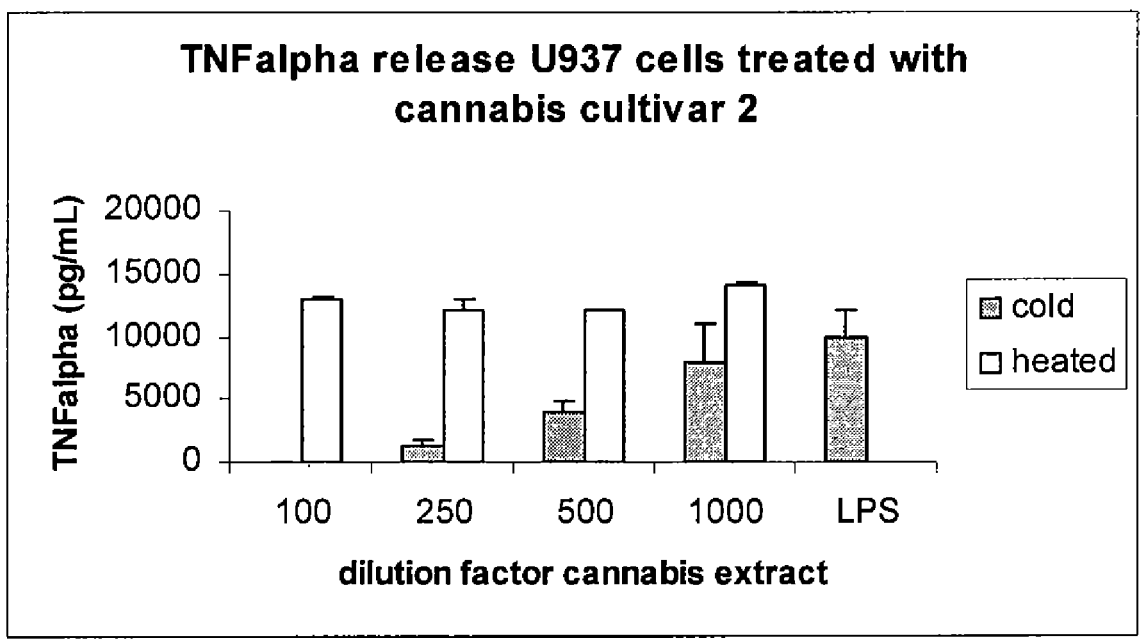
Figure 2B

MEDICINAL ACIDIC CANNABINOIDS

RELATED APPLICATION(S)

This application is a continuation of PCT application no. PCT/NL2005/000075, designating the United States and filed Feb. 2, 2005; which claims the benefit of the filing date of European application no. EP 04075300.6, filed Feb. 2, 2004; both of which are hereby incorporated herein by reference in their entirety.

FIELD OF THE INVENTION

The invention relates to an acidic cannabinoid for medical use and to a cannabis extract comprising an acidic cannabinoid.

BACKGROUND OF THE INVENTION $\Delta^9$-Tetrahydrocannabinol (THC) is naturally found in cannabis. THC has been reported to have use as an analgesic, for instance for patients suffering from rheumatoid arthritis. A side effect of THC is its psychoactive activity. Further, conventionally THC is administered by smoking, which may be detrimental to general health, in particular to the lungs and the coronary system.

WO 89/01332 describes an acidic metabolite of THC, wherein the methyl group at the 9-position, a major metabolite formed in humans and other mammals, is substituted by a carboxyl group. This metabolite is reported to be non-psychoactive. Its use as a therapeutic agent for such purposes as the treatment of chronic pain and tissue inflammation often associated with illnesses such as rheumatoid arthritis is suggested. The Examples show a mouse hot plate test for analgesia, which indicates that, in mice, the metabolite shows about the same analgesic activity as THC and a somewhat lower activity than Naproxen. The Examples further indicate that the metabolite does not induce the formation of gastric lesions in an animal test under conditions wherein aspirin does.

In a review by Bhargava (*Gen. Pharmac.* (1978) 9(4):195-213), potential uses of cannabinoids are mentioned in rather general terms. Bhargava mentions that several cannabinoids have been pharmacologically tested, without disclosing in any detail, a specific medical activity for carboxylated THCs (THC acids), such as $\Delta^9$-tetrahydrocannabinolic acid or the like. In addition, reference is made to the analgesic activity of THC and several other cannabinoids compared to morphine. THC is reported to perform equi-analgesic with morphine, but other tested cannabinoids are reported to be much less potent or even inactive.

Williamson and Evans (*Drugs* 2000, December 60(6): 1303-1314 discuss in general terms a potential clinical use of cannabis. The specific use of THC acids, such as $\Delta^9$-tetrahydrocannabinolic acid or the like, as the active pharmaceutical ingredient, is not disclosed.

GB-A 2 384 707 relates to the use of a cannabinoid acid, in particular cannabidiol (CBD) and cannabidiol acid (CBDA) for use as an active pharmaceutical substance in the treatment of nausea, vomiting, emisis and motion sickness. The compounds may be obtained by extraction from cannabis. As a result of the extraction, relatively small amounts of THC-acids may be present in the extract, but the use of a THC-acid as an active pharmaceutical substance is not mentioned.

SUMMARY

There remains a continuing desire for alternative therapeutics. It is therefore an object of the invention to provide such a therapeutic.

Surprisingly, it has now been found that a specific precursor of THC has properties which are of interest to medical use, such as analgesic and/or anti-inflammatory properties. Accordingly, the present invention relates to an acidic THC precursor for medical use.

More in particular, the present invention relates to an acidic cannabinoid represented by formula Ia or Ib for use as a medicament

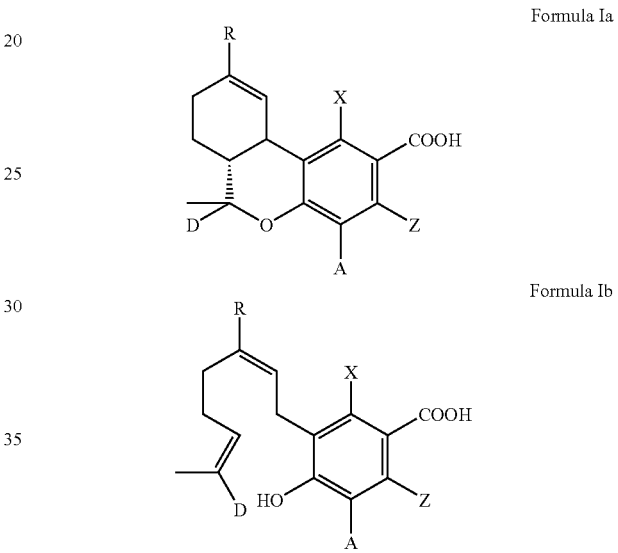

In these formulae X, Z and A each represent a different group selected from the groups —OH, hydrogen and a first alkyl; accordingly, each of these four groups are present in the compound. The first alkyl is preferably a C1-C10 linear or branched alkyl, more preferably a C4-C7 linear or branched alkyl, even more preferably n-pentyl. The first alkyl is preferably Z.

D represents —OH or alkyl, preferably a C1-C3 linear or branched alkyl, in particular a methyl.

R represents a hydrogen, a $C_nH_{2n}$—OH, a $C_nH_{n2}$—COOH or a second alkyl; The n in these groups is an integer, preferably 0, 1 or 2. R is preferably a C1-C3 linear or branched alkyl, more preferably —CH₃.

BRIEF DESCRIPTION OF THE DRAWINGS

FIGS. 2A and 2B show the effect of treatment with a cannabis extract comprising THC-A on the release of TNF-α in an ELISA assay.

DETAILED DESCRIPTION OF THE INVENTION

Figure 1:
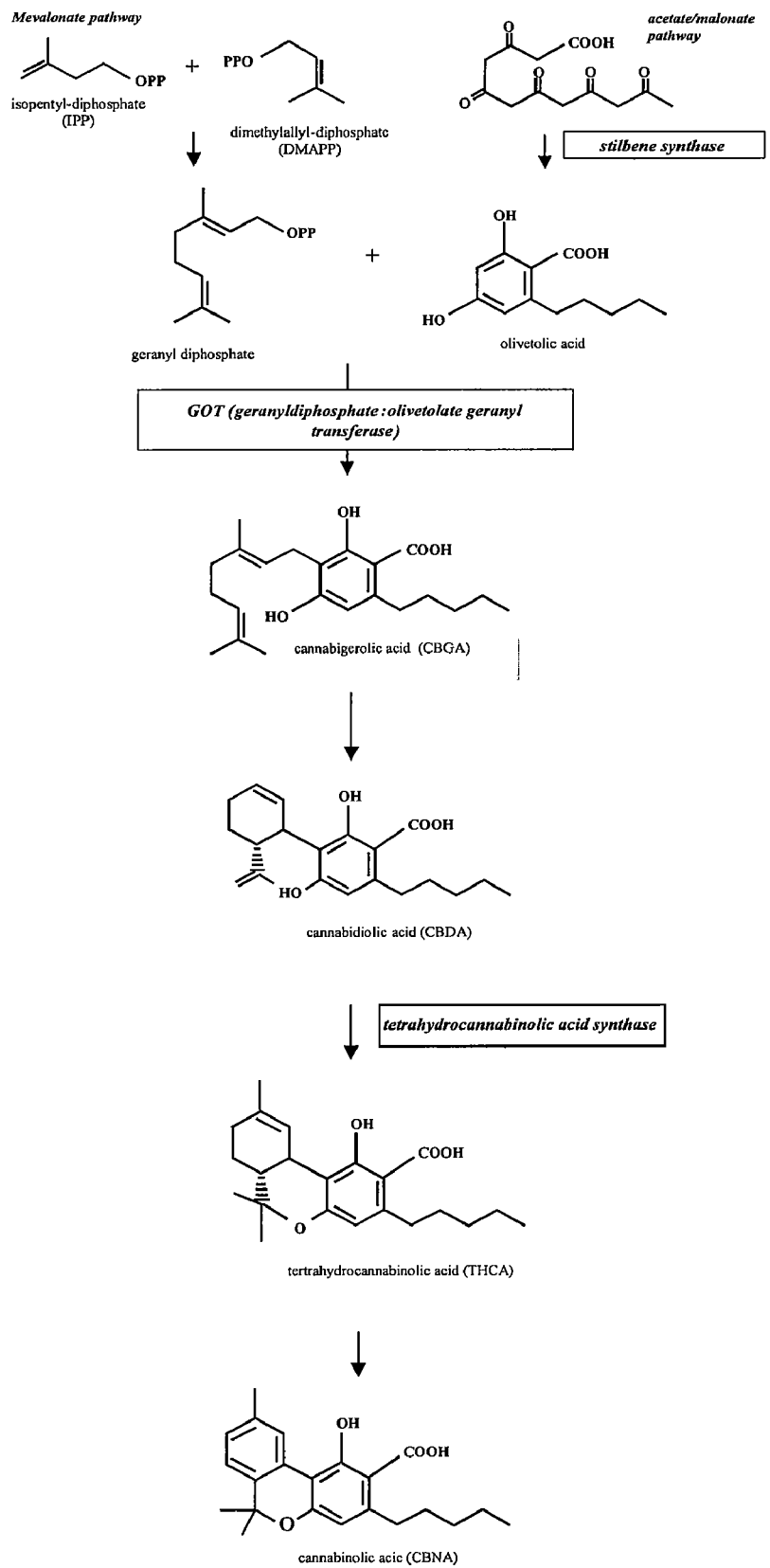
FIG. 1 shows a cannabinoid biosynthetic pathway.

Within the context of the invention, the term "acidic" is used to describe a compound having a carboxyl group, unless specified otherwise. In general, an acidic precursor of THC is transformable into THC by decarboxylation, optionally in combination with one or more other reactions, such as a cyclisation of a precursor having two of the rings forming the core of the THC to form the third ring, (de)alkylation, (de)hydroxylation and the like. Besides the compounds of formula Ia and of Ib, examples of acidic THC precursors are cannabidiolic acid (CBDA), cannabichromenic acid (CBCA), cannabinorolic acid (CBNRA), cannabigerolic acid (CBGA), cannabinolic acid (CBNA) and functional and structural analogues thereof. A number of these compounds are shown in the pathway displayed in FIG. 1.

A compound according to the present invention has been found to have analgesic and/or anti-inflammatory activity. This is surprising, as this finding is contrary from what may be concluded from a standard receptor binding test wherein the dissociation constants ($K_d$) were determined for binding of the compounds to the cannabinoid receptors CB1 and CB2 and compared with the binding of THC (See Examples).

In particular, an acidic compound according to the invention may be used for relieving pain and/or for suppression of an inflammatory response, preferably for modulating the release of one or more inflammatory mediators, in particular cytokine(s), in an animal, preferably in a human.

In a highly preferred embodiment the acidic compound is used to suppress the release of one or more pro-inflammatory cytokines, in particular TNF-α (tumour necrosis factor α), and/or to stimulate the release of anti-inflammatory cytokines, in particular interleukins, more in particular interleukin-10 (IL-10). A compound or composition that can both suppress the release of a pro-inflammatory cytokine and stimulate the release of an anti-inflammatory cytokine, as is provided by the present invention, is of considerable interest to the pharmaceutical industry, and medical science.

An acidic compound according to the invention may for instance be used for (prophylactic or therapeutic) treatment of an animal, preferably a human, against an inflammation, an auto-immune disease or an infection. It may also be used to alleviate symptoms, such as pain or nausea, accompanied with a disease.

In particular, a compound may be used in accordance with the invention for the treatment of a disease selected from the group consisting of multiple sclerosis, arthritis, arthrosis and other inflammatory diseases of bone and/or joint, encephalomyelitis (in particular autoimmune encephalomyelitis), AIDS, inflammatory bowel disease, Crohn's disease, inflammatory skin diseases (dermatitis, Psoriasis) and alleviated symptoms associated with cancer, anorexia, AIDS, spasticity, glaucoma and chronic pain.

Further, it has been found that a compound according to the invention is only lowly psychoactive or even non-psychoactive. Besides, it is expected that the risk for gastro-intestinal damage as a result of using a compound according to the invention is low, and in particular less than for at least some commercially very successful drugs, e.g. aspirin.

Particularly good results have been achieved with an acidic cannabinoid according to Formula Ia or Ib, more in particular a compound according to Formula Ia, wherein Z represents the alkyl and X represents the OH and with an acidic cannabinoid according to Formula Ia or Ib, more in particular a compound according to Formula Ia wherein A the hydrogen. In the presence of such a compound it has been found that the suppression of an inflammatory response, as indicated by its capacity for suppressing TNF-α release, is high in comparison to THC, whilst having no noticeable detrimental psychoactive side effect. Of these compounds $\Delta^9$-tetrahydrocannabinolic acid (THC-A), is particularly preferred. This compound is represented by Formula Ia, wherein Z represents n-pentyl, X is —OH, A is hydrogen, D is methyl and R is methyl. Of this compound in particular, it has surprisingly been found that it is capable of both suppressing a pro-inflammatory cytokine, such as TNF-α, and stimulating an anti-inflammatory cytokine, such as interleukin 10.

In principle, it is possible to synthesise a compound according to the invention (bio)chemically. The skilled person will know how to perform such synthesis based upon common general knowledge and the present disclosure.

It is however an advantage of the invention that an acidic cannabinoid—in particular a compound wherein the first alkyl at the aromatic ring is n-pentyl (such as Z in formula Ia or Ib, or in the equivalent position in an acidic precursor of THC in general)—may be derived from a natural source, such as cannabis. An acidic cannabinoid can be used (to treat a medical indication) directly without further chemical modifications, such as decarboxylising the compound into THC and subsequently metabolising the THC.

A compound according to the invention may be used in isolated form or in an extract from a natural source, in particular from flower tops of cannabis. Particular suitable is a plant or a part thereof, comprising at least 5 wt. % of acidic cannabinoids, e.g. 5-15 wt. %. Very good results have been achieved with *Cannabis sativa, Cannabis indica*. Suitable methods to extract an acidic compound according to the invention are known in the art and include liquid extraction, e.g. with an apolar phase, such as chloroform and a polar phase, in particular an aliphatic alcohol, such as methanol or ethanol. In such an extraction the acidic cannabinoid typically is found in the apolar phase, especially if the extraction procedure is carried out at pH lower than 7. The skilled person will know how to carry out a suitable extraction and further process the acidic cannabinoid, based on common general knowledge and the information disclosed herein. It has been found that an extract according to the invention, comprising an acidic cannabinoid is effective in reducing TNF-α excretion in human macrophages, demonstrating an inhibitory effect of the acidic cannabinoid. In an embodiment, it has further surprisingly been found to be effective in increasing interleukin release too (see Examples).

The preparation of the extract in accordance with the invention is generally carried out under essentially non-decarboxylising conditions to avoid an excessive formation of THC, which may be undesired for its psycho-active side effects and/or for legal reasons, THC at present being illicit in many states. In practice, it is therefore preferred to perform the extraction at a temperature not exceeding 95° C., more preferably at a temperature of less then about 50° C., even more preferably of less than about 25° C. Very good results have been achieved with extraction at a temperature not exceeding about 4° C. The lower limit for the temperature is not particularly critical, as long as the extraction medium remains fluid.

The extract may then be further processed in any way, without excessive exposure to heat to maintain essentially non-decarboxylising conditions and thus avoid excessive formation of THC. In particular such conditions are met if the extract is not excessively exposed to temperatures of about 200° C. or more. Preferably the extract is processed at a temperature not exceeding about 50° C. More preferably any further processing of the extract takes place at a temperature of about 25° C. or less. Accordingly, the solvent of the extract is preferably removed by lyophilisation.

In practice, conditions are considered to be essentially non-decarboxylising heat treatment is considered to be non-excessive when the amount of THC as a percentage of the total dry weight of the extract is less than 5 wt. %, preferably less than 2 wt. %, even more preferably less than 0.5 wt. %. For practical reasons the amount of THC is preferably less than the maximum allowable amount to allow use as a non-prescription medicament, as determined by law. In this respect it is interesting to note that the present invention allows for the preparation of extracts with less than about 0.15 wt. % as a percentage of the dry weight without a need for selective removal of THC from the extract.

THC may be totally absent (i.e. non-determinable by a conventional analytical technique) in an extract or other composition according to the invention. For practical reasons some THC may be present, such as about 0.01 wt. % as a percentage of the dry weight or more.

Good results with respect to its pharmaceutical properties and low side effects have been achieved with an extract or other composition according to the invention wherein the amount of THC as a weight percentage of the amount of the at least one acidic cannabinoid is 0-2 wt. %, preferably less than about 1 wt. %. As indicated above, THC may be absent, although some THC may be present; as such, for practical reasons a preferred lower limit for the amount of THC as a weight percentage of the amount of the at least one acidic cannabinoid is about 0.01 wt. %, more in particular about 0.1 wt. %.

Good results have inter alia been achieved with an extract—in particular a cannabis extract—comprising at least about 10 mg/g based upon the dry weight, preferably at least about 15 mg/g based upon the dry weight, of the acidic cannabinoid. Very good results have been achieved with an extract comprising at least about 20 mg/g based upon the dry weight of the acidic cannabinoid. The upper limit is not particularly critical. For practical reasons the upper limit is preferably about 500 mg/g, more preferably 250 mg/g dry weight.

Preferably, a composition according to the invention, such as a (cannabis) extract, comprises at least one compound selected from the group consisting of cannabidiolic acid (CBD-A), cannabidiol (CBD), cannabigerolic acid (CBGA), cannabigerol (CBG), cannabinolic acid (CBN-A) and cannabinol (CBN), Cannabichromenic acid(CBC-A) and cannabichromene (CBC). In particular in such a composition also comprising a cannabinoid according to formula Ia or Ib, preferably formula Ia, has been found very effective as an anti-inflammatory preparation. The amount of the compounds of this group may be chosen within wide limits. Good results have inter alia been achieved with a composition, in particular an extract, wherein the total amount of CBD and CBD-A is in the range of about 0.01-200%, more in particular about 1-100 wt. % based upon the amount of the at least one acidic cannabinoid. In particular in this range indications exist that synergy occurs.

An extract according to the invention may be employed in any form. It may for instance very suitably be in a dry form or in a liquid form, in particular solubilised in ethanol, water, a vegetable oil or a liquid comprising any of these compounds alone or in a combination.

An extract may very suitably be present in the form of a paste, cream or ointment. Such form is in particular attractive for topical applications, e.g. for treating a dermal inflammation.

An acidic compound or extract according to the invention may very suitably be present in a pharmaceutical preparation, further comprising a pharmaceutically acceptable carrier. A preparation may for instance have the form of a tincture, an ointment, a spray, an inhalant, a powder, a granulate, a suppository, a tablet or a capsule.

Of particular interest is administration as a liquid preparation for oral use or dermal application as a cream or ointment. Applications via the nasal or inhalatory route are in particular attractive for purified acids.

The skilled person will know how to determine a particular dosage regime, depending upon the medical indication, the patients condition and the type of administration.

The invention further relates to a method of treating an animal, preferably a human, with an acidic cannabinoid, which treatment comprises administering the acidic cannabinoid in acidic form. This means in particular that the cannabinoid is administered under essentially non-decarboxylising conditions, in contrast to conventional ways of administering cannabinoids, i.e. by smoking (heating and inhaling) dried flower tops of cannabis plants. Besides avoiding the psycho-active side-effects (as a result of the formation of THC during heating), the present form of administration does not impose any health risks normally associated with smoking. Suitable forms of administration include oral administration (such as ingestion or inhalation) and any other conventional medical ways of administering a medicament.

Accordingly, the invention further relates to the use of an acidic cannabinoid, optionally in the form of an extract or a pharmaceutical preparation as described herein, in the manufacture of a medicament for administration of the cannabinoid in acidic form.

The invention will now be illustrated by the following examples.

EXAMPLES

Example 1

Preparation of the Extracts

Flower tops of three cannabis varieties belonging to *C. sativa* or *C. indica* and hybrids. were used to make extracts. The flower tops were deep-frozen immediately after harvesting and thereafter lyophilised, shortly before extraction.

700 mg dried flower tops were extracted twice with 20 mL chloroform/methanol (1:9), according to the following procedure:

700 mg flower tops were mixed with 18 ml Methanol and sonicated for 5 minutes. 2 mL chloroform were added after which the mixture was sonicated again for 5 minutes. Extraction was then performed (60 minutes 4° C., shaking 250 rpm). Supernatant was removed and the extraction was repeated with the remaining plant-pellet. Both supernatants were pooled and stored at −20° C. until measurements started.

Composition of the Unheated Extracts

The concentration of THC-A, CBD (the total of cannabidiolic acid and cannabidiol) CBN and THC was determined with LC/MS-MS.

The results are shown in Table 1.

TABLE 1

| Extract | THC-A | THC | CBD | CBN |
|---|---|---|---|---|
| | | all concentrations in mg per gram dry weight. | | |
| cultivar 1 | 202 | 1.43 | 0.21 | <0.00005 |
| cultivar 2 | 184 | 1.14 | 0.16 | <0.00005 |
| cultivar 3 | 16.0 | 0.11 | 14.86 | <0.00005 |

Example 2

Receptor Binding Studies

The affinity of the three extracts for binding to the cannabinoid receptors CB1 and CB2 was determined in a receptor binding study. Herein a competitive assay was used between the components of the extracts and tritium labelled ligand CP55,940. The receptors were recombinant human CB1 and CB2 co-expressed with Gαiβ1γ proteins in Sf9 cells In the binding studies, unheated extracts were compared with extracts heat at 200 C to decarboxylate the THC-A. The affinity constants ($K_d$) are shown in Table 2.

TABLE 2

| Extract | $K_d$ CB1 [μM] | $K_d$ CB2 [μM] |
| --- | --- | --- |
| Cultivar 1 unheated | >1 | >1 |
| Cultivar 2 unheated | >1 | >1 |
| Cultivar 3 unheated | >1 | >1 |
| Cultivar 1 heated | 0.0062 | 0.019 |
| Cultivar 2 heated | 0.0079 | 0.021 |
| Cultivar 3 heated | 0.017 | 0.023 |

A compound with a low $K_d$ is generally considered as a potential anti-inflammatory agent or as a potential analgesic. From the much higher $K_d$ values from the unheated (undecarboxylated) extract, one would expect that the acidic cannabinoids would not be promising agents for pain relieve or anti-inflammatory activity.

To confirm that the difference in affinity can be assigned to the cannabinoids the experiments were repeated with the purified components (obtained by fractionation on a Hypersil 10 C18 column, 250×10 mm, 10 micron with 50×10 mm precolumn, Phenomenex)

The results are shown in Table 3.

TABLE 3

| Extract | $K_d$ CB1 [μM] | $K_d$ CB2 [μM] |
| --- | --- | --- |
| THC-A | >1 | >1 |
| THC | 0.0038 | 0.0032 |
| CBD | 0.66 | 0.28 |
| CBN* | (0.036) | (0.017) |

*the CBN was found to be contaminated with THC

Thus, based upon the binding studies it appeared that the precursors of THC, in particular acidic cannabinoids such as THC-A, were not a promising compound for medical use.

Example 3

Biological Immuno-system Based Assay

U937 monocytes (described e.g. in Izeboud et al., *J. Rec. Sign. Tr. Research* (1999), 19(1-4):191-202) were differentiated into macrophages by treating the monocytes for 16 hours with phorbol myristate acetate (PMA)

After 48 hours storage of the macrophages in RPMI-1640 culture medium wherein the medium was replaced every 24 hours. The macrophages were allowed to recover from PMA treatment for 48 hours, during which culture medium was replaced every 24 hours. At day three after PMA treatment, the macrophages were exposed to lipopolysacharide (LPS) (Sigma-Aldrich, L-2630) The macrophages were exposed to LPS in the presence or absence of the cannabis extracts described above (in methanol). The extracts were tested undiluted and in 2.5-fold, 5-fold, 7.5-fold and 10-fold dilution). In the culture medium the TNF-α level was determined a by specific ELISA test (TNFα Cytoset, Biosource CHC1754). Further, the toxicity of the cannabis extracts was determined with a MTT test (Sigma-Aldrich, M-2128) (also described in Mosmann, *J. Immunol. Meth.* 1983, 55-63).

The results of the TNF-α ELISA indicated that the TNF-α release after treatment with unheated extract was considerably reduced, compared to the control treatment (with an almost complete inhibition of the release for undiluted unheated extract). With the heated extract (wherein the THC-A is decarboxylated), no clear effect on the TNF-α release was seen. This demonstrates that the unheated extracts are generally more potent or at least as potent in suppressing the TNFα as the heated extracts. This is an indication that an acidic precursor such as THC-A is a suitable alternative to THC as an anti-inflammatory agent and potentially more potent than THF and/or carboxylated THF metabolites, reported previously.

The MTT tests further demonstrated that none of the tested extracts were toxic (data not shown.)

The experiment was repeated with extracts from two cannabis cultivars, obtained by the method as described in Example 1. Part of the extracts was heated (typically 7 min. at 200° C.), the remainder was not exposed to a temperature exceeding 25° C. (typically kept refrigerated. Heated and unheated extracts were administered in diluted form (100-fold to 1000-fold dilution) to cultures of U937 cells after induction with LPS (as described above).

THC and THC-A concentrations were as shown in Table 4:

TABLE 4

|  | THC (mg/mL) | THC-acid (mg/mL) |
| --- | --- | --- |
| Cultivar 1 heated | 4.81 | 0.12 |
| Cultivar 1 unheated | 0.04 | 5.05 |
| Cultivar 2 heated | 4.37 | 0.09 |
| Cultivar 2 unheated | 0.03 | 4.60 |

FIGS. 2A and 2B show that a considerable reduction in TNF-α was achieved with all unheated extracts (rich in THC-A), with an (almost) complete inhibition at the 100-fold dilution. In contrast, the treatment with the heated extracts (rich in THC) did not result in a reduction of the TNF-α release. This demonstrates the potency of an extract according to the invention for the treatment of an inflammation, in particular an extract obtainable by extraction under conditions at which decarboxylation is avoided, such as by extraction at a temperature below 25° C., more in particular at a temperature of about 4° C. or less.

Example 4

Effect of Acidic Cannabinoid on Pro-inflammatory and Anti-inflammatory Cytokines THC-acid was able to decrease the mRNA levels coding for TNF-alpha in isolated and cultured Peripheral Blood Mononuclear Cells (PBMC) that were stimulated by PHA (phytohemagglutinin). By stimulation with PHA, a response is induced that resembles an inflammatory reaction. TNF-alpha is known as a pro-inflammatory cytokine that is released during the initial stages of inflammation.

In the same study, the levels of mRNA coding for interleukin-10 (IL-10) were increased. IL-10 is known as an anti-inflammatory cytokine. The experimental design of the study was as follows:

PBMC were prepared as described by Visser et al. (J. Investigative Medicine, 49 (2), 2001). In 6-wells plates, each well was filled with 2.5 mL PBMC's ($2\times10^6$ cells in IMDM (Isocoves modified Dulbecco's medium + glutamax, containing $5\times10^{-5}$M 2-mercaptoethanol, 100 U/mL penicillin, 100 U/mL streptomycin and 10% fetal calf serum)) together with 500 µL THC-acid (or medium as control) and 500 µL PHA (or medium as control) After incubation for 4 days (at 37° C.), total RNA was isolated by using Trizol™ according manufactures protocol. From isolated RNA, cDNA was synthesized by using *Promega Reverse Transcription System* according to manufactures protocol.

Figure 3A:
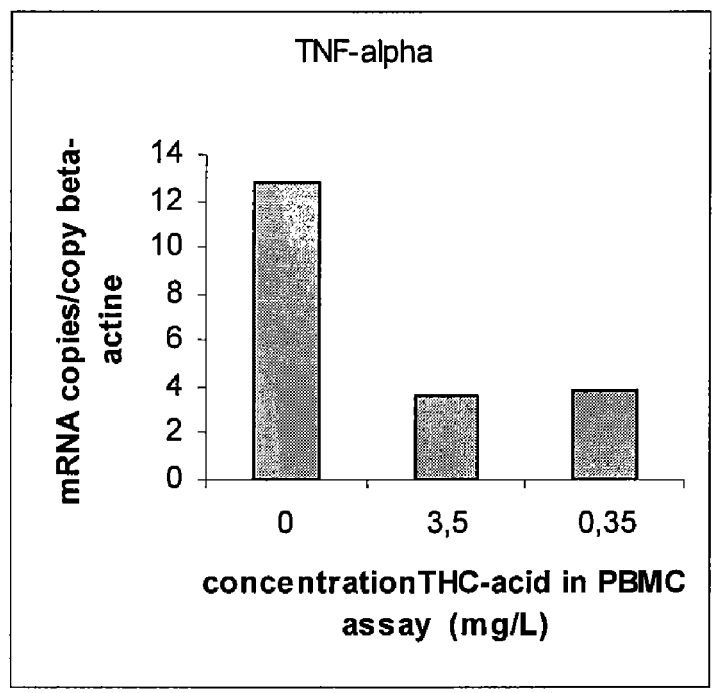
FIGS. 3A and 3B show respectively the inhibitory effect on TNF-α release and the stimulatory effect on interleukin-10 release of an unheated cannabis extract comprising THC-A
Figure 3B:
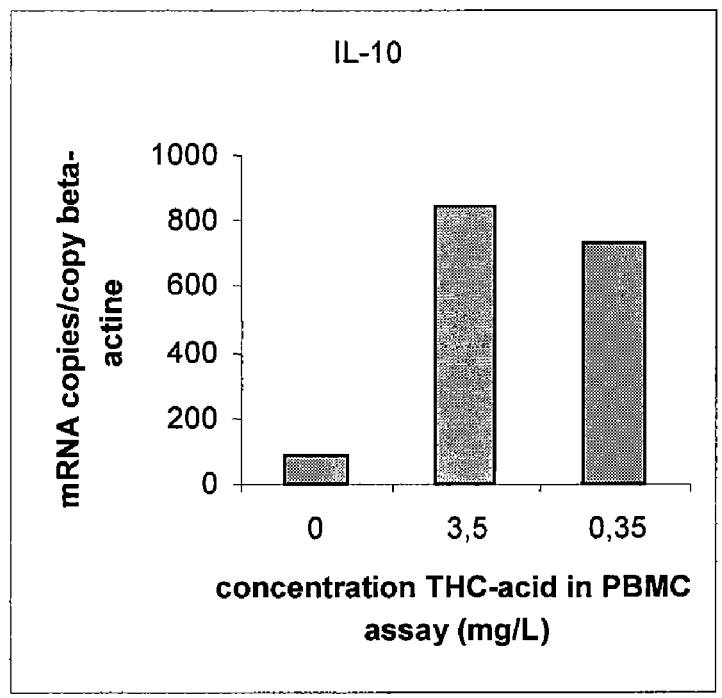

The levels of cDNA were determined by means of Real Time (RT)-PCR using Taqman® Gene Expression assay (Applied Biosystems) according to manufactures protocol. From the levels of cDNA, the amount of mRNA-copies as original present in the PBMC's was calculated as compared to the housekeeping gene β-actine. The presence of THC-acid during incubation resulted in both a decrease in the level of the pro-inflammatory cytokine TNFα and an increase in the level of the anti-inflammatory cytokine IL-10 (see FIGS. 3A and 3B).These results further support the potential of THC-acid to inhibit inflammation.

Example 5

In Vivo Study of Use of Acidic Cannabinoid in the Treatment of Encephalomyelitis The effect of purified THC-acid and unheated cannabis extracts were tested in vivo in a mouse model for Experimental Autoimmune Encephalomyelitis.

In a randomized study (10 mice for each treatment) the disease was induced in 9 weeks old female SJL mice (Harlan) after immunization with the proteolipid-protein as described by Nagelkerken et al. ("Interactions Do Not Play a Major Role in Inhibition of Experimental Autoimmune Encephalomyelitis by Anti-CD154 Monoclonal Antibodies," *J. Immunol*, 173:993-999, 2004). Between day 0 and day 20 after onset of the disease the mice were treated daily with a specified oral dose of THC-acid or unheated extract according to the following scheme:

Group 1: vehicle (0.2 mL olive oil/day);
Group 2: 1 mg purified THC-acid in 0.2 mL olive oil/day;
Group 3: unheated cannabis extract in 0.2 mL olive oil containing 1 mg THC-acid/day.

The severity of the disease was followed during 42 days after onset of the disease by means of clinical behaviour and body weight (as described by Nagelkerken et al. ("Interactions Do Not Play a Major Role in Inhibition of Experimental Autoimmune Encephalomyelitis by Anti-CD 154 Monoclonal Antibodies," *J. Immunol.*, 173:993-999, 2004). After 42 days, the mice were sacrificed and the effect on the brainstem was studied. Treatment with 1 mg purified THC-acid or the unheated cannabis extract containing 1 mg THC-acid reduced the number of inflammatory cells in the brain stem significantly as compared to vehicle.

Figure 4:
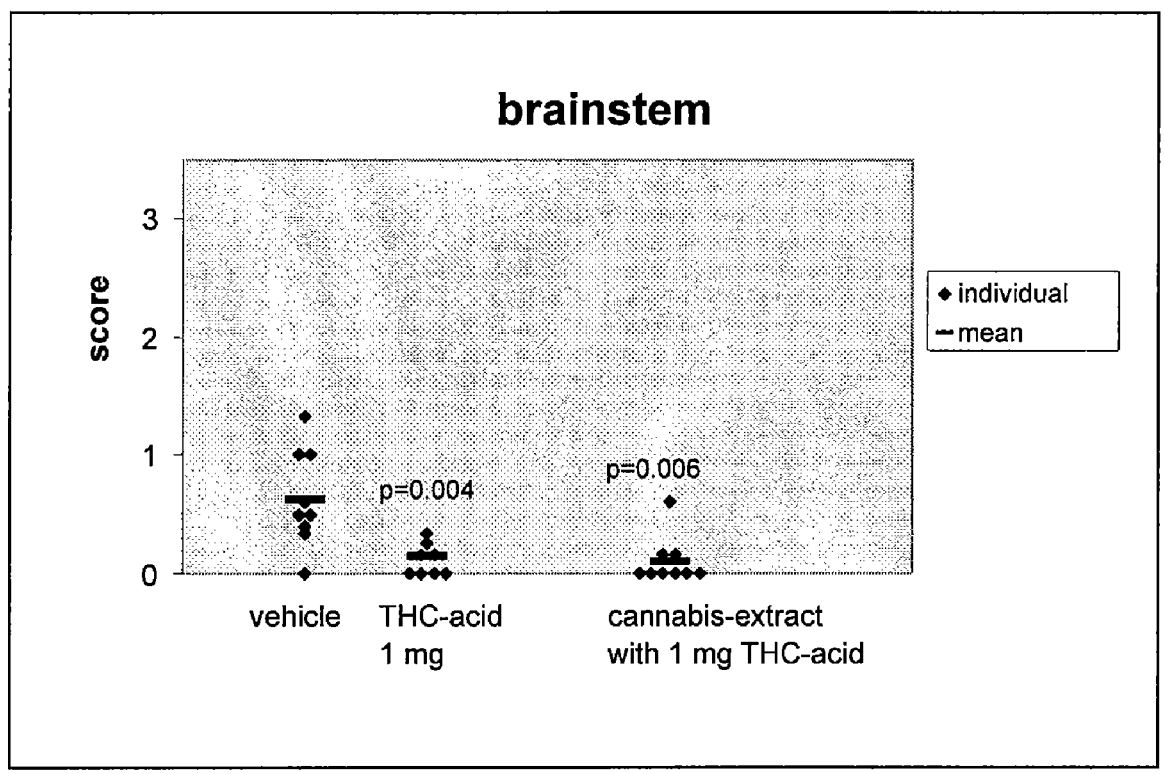
FIG. 4 shows the effect of treatment with (an extract comprising) THC-A in mice suffering from autoimmune encephalomyelitis.

Moreover, as shown in FIG. 4, treatment with 1 mg THC-acid or unheated cannabis extract improved the clinical score significantly. The scores as shown in FIG. 4 are defined as:

0: no infiltrates
1: mild perivascular accumulation
2: mild perivascular accumulation, multi-focal
3: perivascular accumulation, multiple cell layers, multi-focal.

The results in this experiment further indicate that the unheated extract tends to be more effective than the purified THC-A (the median score of the experiments with the extract being 0). Based upon this indication a multivariant analysis was performed, to verify whether other components in the extract are likely to positively contribute to the treatment. From the results of the multivariant analysis, it was apparent that this indeed was the case (results not shown).

The invention claimed is:

1. A method for relieving pain, comprising administering a therapeutically effective amount of a plant extract including tetrahydrocannabinolic acid as an active ingredient in an amount of at least about 10 mg/g based on the dry weight of the plant extract, to an animal in need of pain relief, wherein the plant extract includes between 0 to 2 wt % tetrahydrocannabinol.

2. A method for suppressing an inflammatory response, comprising administering a therapeutically effective amount of a plant extract including tetrahydrocannabinolic acid as an active ingredient in an amount of at least about 10 mg/g based on the dry weight of the plant extract, to an animal in need of inflammatory response suppression, wherein the plant extract includes between 0 to 2 wt % tetrahydrocannabinol.

3. A method for treating a disease, comprising administering a therapeutically effective amount of a plant extract including tetrahydrocannabinolic acid as an active ingredient in an amount of at least about 10 mg/g based on the dry weight of the plant extract, to an animal in need of such treatment; wherein the disease is selected from the group consisting of inflammations, autoimmune diseases and symptoms associated with such diseases, wherein the plant extract includes between 0 to 2 wt % tetrahydrocannabinol.

4. The method of claim 2, wherein the tetrahydrocannabinolic acid suppresses the release of a pro-inflammatory cytokine and/or stimulates the release of an anti-inflammatory cytokine.

5. The method of claim 2, wherein the tetrahydrocannabinolic acid suppresses the release of TNF-α.

6. The method of claim 2, wherein the tetrahydrocannabinolic acid stimulates the release of interleukin-10.

7. A method for treating a disease or alleviating the symptoms of a disease, comprising administering a therapeutically effective amount of a plant extract including tetrahydrocannabinolic acid as an active ingredient in an amount of at least about 10 mg/g based on the dry weight of the plant extract, to an animal in need of such treatment; wherein the disease to be treated is inflammatory skin disease or encephalomyelitis; and wherein the plant extract includes between 0 to 2 wt % tetrahydrocannabinol.

8. A method for treating an autoimmune disease comprising administering a therapeutically effective amount of a plant extract including tetrahydrocannabinolic acid as an active ingredient in an amount of at least about 10 mg/g based on the dry weight of the plant extract, to an animal in need of such treatment, wherein the plant extract includes less than 2 wt % tetrahydrocannabinol.

9. A method for treating encephalomyelitis comprising administering a therapeutically effective amount of a plant extract including tetrahydrocannabinolic acid as an active ingredient in an amount of at least about 10 mg/g based on the dry weight of the plant extract, to an animal in need of such treatment, wherein the plant extract includes less than 2 wt % tetrahydrocannabinol.

10. A method according to claim 1 wherein the animal is a human.

11. A method according to claim 2 wherein the animal is a human.

12. A method according to claim 3 wherein the animal is a human.

13. A method according to claim 7 wherein the animal is a human.

14. A method according to claim 8 wherein the animal is a human.

15. A method according to claim 9 wherein the animal is a human.

* * * * *